United States Patent
Gallas et al.

(10) Patent No.: US 10,357,124 B2
(45) Date of Patent: Jul. 23, 2019

(54) COMPOUND, COMPOSITION, AND METHOD FOR PROTECTING SKIN FROM HIGH ENERGY VISIBLE LIGHT

(71) Applicant: Photoprotective Technologies, Inc., San Antonio, TX (US)

(72) Inventors: James Gallas, San Antonio, TX (US); Nava Dayan, Fair Lawn, NJ (US)

( * ) Notice: Subject to any disclaimer, the term of this patent is extended or adjusted under 35 U.S.C. 154(b) by 0 days.

(21) Appl. No.: 14/701,510

(22) Filed: Apr. 30, 2015

(65) Prior Publication Data

US 2016/0317425 A1 Nov. 3, 2016

(51) Int. Cl.
| | |
|---|---|
| *A61K 8/84* | (2006.01) |
| *A47G 33/06* | (2006.01) |
| *A61Q 19/08* | (2006.01) |
| *A61Q 17/04* | (2006.01) |
| *A61K 8/72* | (2006.01) |
| *F21S 4/10* | (2016.01) |
| *A61K 8/49* | (2006.01) |
| *A61Q 1/02* | (2006.01) |
| *A61Q 19/00* | (2006.01) |

(52) U.S. Cl.
CPC .............. *A47G 33/06* (2013.01); *A61K 8/49* (2013.01); *A61K 8/72* (2013.01); *A61Q 17/04* (2013.01); *A61Q 19/08* (2013.01); *F21S 4/10* (2016.01); *A61Q 1/02* (2013.01); *A61Q 19/007* (2013.01)

(58) Field of Classification Search
CPC .......... A61Q 19/08; A61Q 1/02; A61Q 17/04; A61K 8/72
USPC .......................................................... 424/59
See application file for complete search history.

(56) References Cited

U.S. PATENT DOCUMENTS

| | | | | |
|---|---|---|---|---|
| 5,709,847 A | * | 1/1998 | Bissett ..................... | A61K 8/44 424/400 |
| 8,048,343 B2 | * | 11/2011 | Gallas .................... | G02B 1/041 210/656 |
| 2006/0282066 A1 | * | 12/2006 | Gallas .................... | G02B 1/041 606/9 |
| 2013/0078205 A1 | * | 3/2013 | Dayan ...................... | A61K 8/72 424/60 |

* cited by examiner

*Primary Examiner* — Yanzhi Zhang (57) ABSTRACT

A compound, composition, and method for the protection of skin from the harmful effects of radiation, and particularly the harmful effects of high energy visible (HEV) radiation, are disclosed. The compound is a melanin derivative that can be formulated into compositions containing the melanin derivative and a suitable carrier. The composition is topically applied to the skin to reduce the risk of photoaging and improve skin repair due to damage from radiation.

5 Claims, 2 Drawing Sheets

Figure 2

COMPOUND, COMPOSITION, AND METHOD FOR PROTECTING SKIN FROM HIGH ENERGY VISIBLE LIGHT

RELATED APPLICATIONS

This application is a continuation application of co-pending U.S. patent application Ser. No. 13/582,817 filed on Dec. 7, 2012 which is the national stage of PCT/US11/26982 filed on Mar. 3, 2011 which claims the benefit of U.S. provisional patent application No. 61/313,456, filed Mar. 12, 2010, incorporated herein by reference in its entirety.

TECHNICAL FIELD OF THE INVENTION

The present invention relates to the protection of skin from the harmful effects of high energy visible (HEV) light. More particularly, the present invention relates to a melanin derivative that reduces the risk of skin photoaging attributed to HEV light, and that overcomes a delay in the repair of skin damage attributed to sunlight and retards photodamage and photoaging of the skin. The melanin derivative can be formulated into a variety of topically-applied skin care compositions, including sunscreen compositions.

BACKGROUND OF THE INVENTION

The skin care industry has long recognized that sunlight exposure increases the risk of wrinkles, age spots, and skin sagging. Such skin damage is photochemical in nature and is associated with high energy, short wavelength light. This light leads to undesirable biochemical changes, such as inflammation and DNA and cell organelle damage. Until the 1970s, the skin care industry considered filtration of UVB radiation sufficient to protect the skin against photo-damage from sunlight exposure. The basis for this conclusion was that a) UVB alone causes redness of the skin (erythema) and b) among the wavelengths of radiation reaching the earth, the region between 280 nm and 320 nm (i.e., UVB) is the most energetic, and thereby the most damaging. A sunscreen active ingredient therefore has been defined as an ingredient that absorbs at least 85 percent of the light in the UV range at wavelengths from 280 to 320 nanometers, but transmits UV light at wavelengths longer than 320 nanometers.

More recently, the skin care industry position regarding photo-damage evolved to include protection against longer-wavelength UVA radiation (320 nm to 400 nm) in addition to protection against UVB. It has been known for some time that UVB, while enabling the skin to produce vitamin $D_3$, nevertheless also produces erythema (sunburn). If the UVB radiation reaches a threshold dose level termed the minimum erythemal dose (MED), sufficient UVB radiation has been delivered to the skin to cause visible erythema. UVA radiation is orders of magnitude less erythmogenic than UVB radiation, but is nevertheless damaging to the skin. The basis for this position was evidence of DNA damage caused by UVA wavelengths that penetrate deeper into the skin. Therefore, with regard to photodamage to skin from the sun, the prevailing view is that both UVB and UVA radiation should be blocked to prevent damage to the skin.

When considering the effects of UV radiation on the skin, the range of UV wavelengths therefore can be divided into UVA (400-320 nm), also called Long Wave or black light, and UVB (320-280 nm), also called Medium Wave. UVB radiation and UVA radiation both exist in solar light. UVB radiation affects the outer layer of the skin. UVA radiation penetrates deeply into the skin and does not cause sunburn. UVA however can contribute to the aging of skin, DNA damage, and possibly skin cancer. Both UVA and UVB wavelengths can damage collagen fibers. This damage contributes to photo-aging of human skin, which can be reduced by blocking these wavelengths of solar radiation.

The protection of skin from fluorescent lighting also has been suggested (V. Beral, The Lancet, Volume 320, Issue 8293, pages 290-293 (1982).). Although fluorescent light bulbs generally have not been considered to pose a significant UV hazard. Recent studies show significant variation in the spectral output of UV light emissions from 19 different compact fluorescent light bulbs, even within the same class. Although the power output from any given bulb is low, the possible exposure time on a daily basis can be relatively high. The results of the study indicate a potential daily UV dose that ranges from 0.1 to 625 mJ cm.sup.-2, and a daily dose of UVB that ranges from 0.01 to 15 mJ cm.sup.-2. It therefore was concluded that because individuals are exposed to these UV intensities for long periods of time, significant cumulative damage could occur (R. S. Klein et al., Photochemistry and Photobiology, Volume 85, Issue 4, pages 1004-1010, July/August 2009).

UVB sunscreens are evaluated by their ability to prevent erythema, which is how the Sun Protection Factor (SPF) is typically defined. Because UVA radiation does not redden the skin (erythema), its damaging effects cannot be determined by current SPF testing. However, UVA light, because of its longer wavelength, can penetrate deeper into the skin than UVB light and is theorized to be a prime cause of wrinkles. Although, to date, no validated clinical measurement exists to test for the health benefits of blocking UVA radiation, it is important that both UVA and UVB radiation are blocked from the skin.

Present sunscreen formulations typically include a mixture of compounds for absorbing UVA and UVB radiation. Commercially approved formulations include a UVB blocker, such as a p-methoxycinnamate or an aminobenzoate, and a UVA blocker, such as a benzone or an anthranilate. These compounds generally absorb an incoming UV photon and reradiate a lower energy photon. While typically less esthetic, physical blockers, such as zinc oxide, generally provide better screening of light.

Research therefore has focused on UVB and UVA radiation with respect to interaction of sunlight with the skin. However, limiting research efforts to the UVB and UVA wavelength ranges neglects the potential of skin damage from longer wavelength radiation, such as damage caused by visual light (400 nm-700 nm), like premature skin aging and skin cancer. For example, when assessing SPF, wavelengths outside of the UVB-UVA range (290-400 nm) are not tested, thereby missing the deleterious effects of visible and near-infrared wavelengths on the skin.

High energy visible (HEV) light is high frequency light in the violet/blue band from 400 nm to 500 nm in the visible spectrum (400 nm-700 nm). The effect of HEV light on macular degeneration was studied and HEV light has been implicated as a cause in this age related disorder (Glazer-Hockstein et al., Retina 26(1) (2006) pages 1-4). The mechanism by which HEV light damages the lens and the retina is believed to be an accumulation of reactive oxygen species (ROS) due to oxidative damage to cells and their organelles. These changes are irreversible, and therefore should be attenuated and/or prevented. Two recently published studies, conducted to evaluate the effect of HEV light on skin, show that the damaging effects to epidermal and dermal tissue are similar to the damaging effects on the eye (M. Denda et al.

J. Invest. Dermatol. 128 (2008) 1335-1336 and L. Zastrow et al. IFSCC Magazine, 11(3) (2008) 297-315).

One recent study (M. Denda et al.) showed that visible radiation (400-700 nm) of different wavelength ranges has different effects on the skin barrier recovery rate of hairless mice after barrier disruption. It was found that blue light (450-500 nm) delayed barrier recovery compared to a control kept in the dark. In particular, the skin barrier repair rate a) decreased with exposure to blue light; b) did not change with green light; and c) increased with red light. The barrier recovery was measured by means of transepidermal water loss (TEWL). In the same study, culture sections of hairless mousse skin were exposed to the same wavelengths. Electron microscopy evaluation revealed that the irradiated skin showed different morphology compared to control skin kept in the dark. It demonstrated a depleted content of intercellular lipids between the stratum corneum (SC) and the stratum granulosum (SG) suggesting the prevention or suppression of processes that support barrier recovery.

The effect of skin exposure to visible light in an ex vivo skin model using human skin obtained from surgery also was studied, and, in particular, the effect of the visible spectra with and without UVA and UVB on the generation of ROS in the skin (L. Zastrow et al.) In this study, high energy (HEV) light in the region of wavelengths between 400 nm and 500 nm that the eye perceives as violet and blue light, contributes significantly to the production of free radicals in the skin. To quantify free radical generation, ESR-X band spectroscopy was utilized. Free radical formation was detected under the influence of all wavelengths from the UVB range to the end of the visible range (280-700 nm). Unexpectedly, the amount of radical formation due to visible light exposure was highly significant. When calculated as part of the spectra of exposure to natural sun light, it showed that UVB generated 4% of ROS, UVA generated 46%, and visible light generated 50% of ROS production. Further identification of the radicals showed that the superoxide anion radical $O_2^-$ and the hydroxyl radical $OH$. were produced. Generation of these two highly reactive species can lead to a chain reaction and generation of other biological radicals, including secondary lipid radicals .CH—R in different skin layers. ROS production is well known to be involved in premature skin aging, often accompanied by inflammatory cascades, generation of age spots and wrinkles, and in the promotion of cancerous skin lesions.

The above studies were conducted independently of one another and led to two conclusions: (a) HEV-light accelerates skin aging by an overexpression of damaging free radicals (at the deep live epidermis and dermis layers) and (b) HEV light leads to a compromised skin barrier (at the stratum corneum and upper live epidermal layers). These two processes are known to be involved in skin aging. Overall, it has been suggested that HEV light causes as much skin damage as UVA and UVB radiation combined.

While the cosmetic and personal care industry has been focusing on the improvement of sun protecting formulations to efficiently block exposure to UVB and UVA light, it has neglected the effects of visible light on the skin and the formulation of compositions that shield the skin from HEV wavelengths. Furthermore, in order to protect the skin from visible light, persons in the art expect that a compound or composition would be dark in color. Providing a darkly colored composition for application to the skin, presents a constraint on consumer acceptance, whereas UV filtration imparts no color to a skin care product. For example, melanin has been disclosed for use in skin care products based upon a) the UV-absorbing character of melanin and b) the fact that melanin is a natural product for protection against sunlight damage. However, the color of such products was not consumer acceptable.

A need therefore exists in the art to provide compounds and compositions that protect skin from HEV light in sunlight and in artificial lighting that contains larger amounts of HEV light. Accordingly, provided herein are novel melanin derivatives having an esthetically acceptable light yellow color in formulated compositions, like skin care products, and that effectively absorb light in the HEV range.

SUMMARY OF THE INVENTION

The present invention is directed to compounds and cosmetic or dermatological compositions used in methods of protecting skin from the harmful effects of sunlight. More particularly, the present invention is directed to compounds and compositions that protect the skin against the harmful effects of HEV light. The compounds and compositions reduce the risk of skin photoaging, and also improve skin repair damage attributed to sunlight and indoor artificial light exposure.

In accordance with the present invention, a melanin derivative capable of blocking HEV sunlight, and that is esthetically acceptable, is incorporated into a cosmetic or dermatological composition for topical application to the skin. A present melanin derivative particularly absorbs light in the 400-500 nm range of the visual spectrum, with minimal absorption in the red range.

Therefore, one embodiment of the present invention is to provide a method of treating skin with a topically applied composition comprising contacting the skin of an individual with a sufficient amount of a present melanin derivative to protect the skin from the harmful effects of HEV radiation, i.e., reduce the risk of sunlight-related skin damage and reduce the risk of photo-damage to the skin.

As used herein, the term 'melanin derivative' means a melanin prepared in a standard way, for example, by auto-oxidation using water as a solvent and oxygen or an oxidizer and controlling the pH, with or without an oxidizer, which then is chemically or physically modified, for example, by bleaching, by selective precipitation, or by fractionation, as disclosed.

Another embodiment of the present invention is to provide a composition comprising about 0.01% to about 15%, by weight, of a melanin derivative and a cosmetically-acceptable carrier. In accordance with the present invention, the melanin derivative is incorporated into a composition suitable for topical application to the skin of a human. The composition can further contain additional formulation ingredients for an efficient and efficacious application of the melanin derivative to the skin. The composition is applied directly to the skin, and is in the form of a cosmetic or dermatological formulation, for example, a solution, a dispersion, an oil-in-water emulsion, a water-in-oil emulsion, stick, spray, foam, or a gel.

Still another embodiment of the present invention is to provide a method of treating human skin comprising applying a composition comprising a present melanin derivative to a surface of the skin. The method reduces the risk of sunlight-related damage and other environmental-related damage to the skin.

Yet another embodiment of the present invention is to provide a composition containing a present melanin derivative and a second topically active compound, and use of the composition as a skin-care product, a topical drug product, or a cosmetic product to protect skin from HEV radiation. The topically applied compositions include, for example, sunscreens, skin lotions, creams, body rinses, topical medicaments, make-up emulsions, foundations, and skin-treatment products.

In yet another embodiment of the present invention, the melanin derivative has a molecular weight of 500 to about 10,000 Daltons and has a low color, e.g., has a yellow color. The melanin derivative is sufficiently hydrophilic and of sufficient molecular weight to minimize skin penetration, and has a sufficiently high blue to red ratio of optical density (OD ratio), i.e., OD (440 nm) to OD (600 nm) ratio, to provide a high HEV absorption and avoid absorption of red light. In one embodiment, an approximately 10 wt % aqueous solution of a present melanin derivative has L*a*b* color scale values of L*—about 89 to about 92, a*—about 0.25 to about 3, and b*—about 40 to about 50.

Another aspect of the present invention is to incorporate a sufficient amount of a present melanin derivative into a composition that further includes a light-sensitive compound in order to stabilize the sensitive compound against light degradation. Typically, the stabilizing amount of the melanin derivative is about 0.001% to about 1%, and preferably about 0.01% to about 0.1%, by weight of the composition.

These and other aspects and novel features of the present invention will become apparent from the following detailed description of the preferred embodiments.

DETAILED DESCRIPTION OF THE PREFERRED EMBODIMENTS

A reduction in the harmful effects of sunlight, e.g., sunburn and skin cancer, occupies greater consumer emphasis today than ever before. The incorporation of UVB and UVA filters in cosmetic products of various types is long standing. For example, skin care and cosmetic products containing known filters, e.g., octocrylene, a benzophenone, homosalate, padimate O, and titanium dioxide, are available commercially. However, such products do not address the harmful effects of radiation outside the UVB and UVA region, e.g., HEV radiation.

Compounds and compositions of the present invention reduce the risk of skin damage from the effects of HEV radiation and help maintain the appearance and condition of the skin. The present compounds and compositions also reduce the risk of photo-damage to the skin and reduce the risk of premature aging of the skin, such as wrinkles and other visual indicia of skin aging, like a loss of skin tone and elasticity.

The present invention is directed to providing compounds and compositions that overcome problems associated with prior compositions used to protect the skin from sunlight. In particular, the present compositions contain a melanin derivative that protects the skin from the effects of HEV radiation.

As used herein, the term "maintains" means that a visual indicia of harm to the skin does not change over time, e.g., the incidence of wrinkles, sagging, skin tone, elasticity, and/or that an indicia of harm to skin does not increase over time, but rather remains relatively constant.

In accordance with the present invention a melanin derivative is used to protect skin against HEV radiation and reduce the risk of sunlight-related skin damage. Melanin is a class of compounds found in plants, animals, and protists, where it serves multiple roles including pigmentation and photoprotection. Melanin from a natural source falls into two general classes: eumelanin, a black-to-dark-brown insoluble material found in human black hair and in the retina of the eye, and pheomelanin, a yellow-to-reddish-brown, alkali-soluble material, found in red hair and red feathers. The most common form of biological melanin is eumelanin, a brown-black polymer of dihydroxyindole, dihydroxyindole carboxylic acid, and their reduced forms. Pheomelanin is a red-brown polymer of benzothiazine units largely responsible for red hair and freckles. Melanins are very complex absorbing materials and are oligomers of the following building blocks, as well as the precursors and the various redox intermediates leading to these building blocks during oligomerization.

Skin coloration is directly related to melanin formation. Melanin is synthesized in melanocytes found in the epidermal basal layer between proliferated keratinocytes before terminal differentiation. Melanin is synthesized enzymatically at roughly 10 nm granular sites studding the internal walls of the melanosome, a roughly 1 .mu.m diameter organelle. Melanosomes can contain a variable amount of melanin. The increased production of melanin in human skin is called melanogenesis, which is stimulated by DNA damage caused by UVB-radiation, and leads to a delayed development of tan skin. Melanin formation is directly related to the action of tyrosinase on tyrosine and cysteine. The more melanin that is produced, the darker the skin color. In humans, melanin is the primary determinant of human skin color and also is found in hair, the pigmented tissue underlying the iris, the medulla and zona reticularis of the adrenal glad, the stria vascularis of the inner ear, and in pigment-bearing neurons within areas of the brain stem, such as the locus ceruleus and the substantia nigra.

In addition to natural melanins, synthetic melanin also can be prepared, for example, as set forth in U.S. Patent Publication No. 2006/028066 and U.S. Pat. No. 5,112,883, each incorporated herein by reference in their entirety. A "melanin" used as a starting material for a present melanin derivative can be any melanin known in the art, including plant derived melanins. The term "melanin" as used herein is not limited to the precursors or the techniques described in this specification and includes, for example, melanins as disclosed in G. Prota, J Invest Dermatol. (1993 February) 100 (2 Suppl): 156S-161S and P. A. Riley, The International Journal of Biochemistry & Cell Biology, Volume 29, Issue 11, November 1997, pages 1235-1239, each incorporated herein by reference in its entirety.

The photophysical properties and biological activity of melanin make it an excellent photoprotectant. Melanin absorbs harmful UV radiation and transforms the energy into harmless amounts of heat. This property enables melanin to dissipate more than 99.9% of the absorbed UV radiation as heat and the generation of free radicals is minimized, This prevents indirect DNA damage which is responsible for the formation of malignant melanomas. Melanin is a very useful pigment for the absorption of high energy visible light because it is able to reduce absorption of violet and blue light without disturbing color perception. However, melanin occurs naturally in different colors (red, yellow, brown) and not all melanins filter HEV light in the same way. Due to its extreme color, melanin has not been used extensively in skin care and personal care products because of the unesthetic appearance of compositions containing melanin and because of the color imparted to skin contacted with melanin.

The present invention therefore is directed to protecting skin from the harmful effects of HEV using a melanin derivative. In particular, the present invention utilizes a melanin derivative that minimally affects the skin tone of individuals using the compound and has the ability to strongly filter HEV radiation, to moderately filter green light, and to transmit red and near infrared (IR) wavelength to the sub-epidermal melanin. A present melanin derivative exhibits minimal absorbance of red and near infrared (NIR) wavelengths, which is a substantial benefit because light in this range of wavelengths is known to be phototherapeutic and provide anti-aging benefits (J. H. Lee et al., Yonsei Medical Journal, 47(4), 485-490 (2006)). A present melanin derivative also is designed to exhibit enhanced hydrophilicity, at least in part through the creation of additional carboxyl groups during its preparation, such that it remains on the skin surface to protect the skin, as opposed to penetrating into the skin.

A present melanin derivative has following properties: (a) a sufficiently high blue to red ratio in optical absorption or optical density (OD), i.e., OD at 440 nm/OD at 600 nm of 10 or greater, to maximize HEV absorption and minimize absorption of red light; (b) a sufficiently high molecular weight of 500 to about 10,000 Daltons to retard penetration of the melanin derivative into the skin and provide for a high deposition on the upper layer of the skin; (c) a sufficiently high degree of hydrophilic character to minimize the skin penetration; and (d) is non-cytotoxic and non-phototoxic.

The present melanin derivatives can be prepared by one or more of bleaching, solvent extraction, and dialysis techniques known in the art, for example in U.S. Patent Publication 2006/0282066, incorporated herein by reference in its entirety.

An approximately 10 wt % solution of a present melanin derivative has L*a*b* color scale values of L*—about 89 to about 92, a*—about 0.25 to about 3, and b*—about 40 to about 53. L*a*b* values characterize the darkness (the L* value) and the color (the a* and the b* values) of a material, and are well known to those skilled in the art. The color analysis is carried out according to the CIELAB method (Hunterlab, Volume 8, 1996, Book 7, pages 1-4) with a "LabScan XE S/N LX17309" colorimeter (Hunterlab, Reston, US). This method describes the colors via the coordinates L, a, and b of a three-dimensional system. L indicates the brightness, where L=0 means black and L=100 white. The values of a and b indicate the positions of the color on the red/green and yellow/blue color axes respectively, wherein +a represents red, −a represents green, +b represents yellow, and −b represents blue.

In particular, a melanin derivative of the present invention can be prepared as set forth in U.S. Patent Publication No. 2006/0282066 and U.S. Pat. No. 5,112,883, each incorporated herein by reference in its entirety, which disclose various methods for synthesizing melanins. In general, one procedure for manufacturing a melanin derivative of the present invention comprises a) synthesis of the melanin; b) purification of the melanin; c) bleaching of the melanin; d) purification of the bleached melanin; and e) fractionation of the bleached melanin into a molecular weight range of between 500 to about 10,000 Daltons, preferably about 2,000 to about 10,000 Daltons, and more preferably about 5,000 to about 10,000 Daltons.

A preferred embodiment of the melanin derivative manufacturing process comprises: a) synthesis of the melanin; b) purification of the melanin; c) fractionation of the bleached melanin into a lower molecular weight intermediate product; d) bleaching of the intermediate melanin; e) purification of the bleached intermediate melanin; and f) fractionation of the bleached intermediate melanin into a molecular weight range of between 500 to about 10,000 Daltons, preferably about 2,000 to about 10,000 Daltons, and more preferably about 5,000 to about 10,000 Daltons.

Example 1 a) Synthesis

The melanin was synthesized as follows: 15 g of L-tyrosine was dissolved in 800 mL of water; 60 g of ammonium persulfate was dissolved in 200 mL of water; 26 g of sodium hydroxide (NaOH) was dissolved in 50 mL of water. The pH was adjusted to 8.5 with sodium hydroxide and the solution stirred for 10 hours.

b) Purification

While stirring, the product was acidified with hydrochloric acid (HCl) to pH 1.5 using approximately 1 L of water. Continue stirring for about 10 minutes and remove stirrer and allow the product to stand for 24 hours. Separate the supernatant; add about 1 liter of deionized water and adjust the pH to 2 with dilute hydrochloric acid while stirring for 10 minutes; allow the product to stand for 24 hours without stirring.

c) Fractionation

Raise the pH to between 3 and 4 while stirring for about 1 hour using sodium hydroxide, stop stirring and allow the product to stand for 24 hours. Separate the supernatant or capture the supernatant by filtration.

d) Bleaching

Increase the concentration of the product to about 2% by evaporation (roto-evaporation and aliquot until a 2% solution by mass) was obtained. Add NaOH to pH 10.5. Heat the product to 45.degree. C. to 50.degree. C. Add sodium persulfate as a powder in a mass ratio of 13:1 (persulfate to melanin). The exothermic reaction was allowed to reach approximately 75.degree. C. and the reaction was stirred overnight at 25.degree. C. to 30.degree. C. Adjust pH to 7.5 with weak acid (HCl) or base (NaOH).

e) Purification

The material then was precipitated by addition of HCl and recovered and purified by centrifugation and washing at pH 2.5. A powder was obtained by vacuum heating at 60.degree. C. A yellow-orange powder was obtained.

f) Second Fractionation

The yellow-orange powder was dissolved in deionized water at a 2% mass concentration and the pH adjusted to 7.5 with sodium hydroxide. The solution was stirred for 24 hours. The pH of the solution then was lowered by a dropwise addition of HCl until aliquots of the solution show light scattering from a red LED light beam. The pH is about 3 to 4. The yellow supernatant was poured off or filtered as a product and concentrated again by acid precipitation at pH 2 or by filtration.

In a second preferred embodiment, an HEV-absorbing melanin derivative is prepared by breaking the conjugation of the melanin structure, either during synthesis, or after synthesis, by derivatization of its surface. A loss of conjugation can be affected by a copolymerization of melanin with a sulfur-containing amino acid, such as L-cysteine. A loss of conjugation also can be affected by treating a melanin with an enzyme, for example tyrosinase, TRP1 (5,6-dihydroxyindole-5-carboxylic acid oxidase), TRP2 (dopachrome tautomerase), and mixtures thereof.

A third embodiment is the preparation of an HEV-absorbing melanin derivative that results from deaggregation of the melanin structure by treating melanin chemically to cause destacking of the 3.4 A-spaced layers, or by incorporation of other precursor molecules that provide steric hindrance so as to preclude stacking. Destacking and also deagglomerization of melanin causes a drop in the red-end absorption of melanin, which is an important aspect of the present invention.

Figure 1:
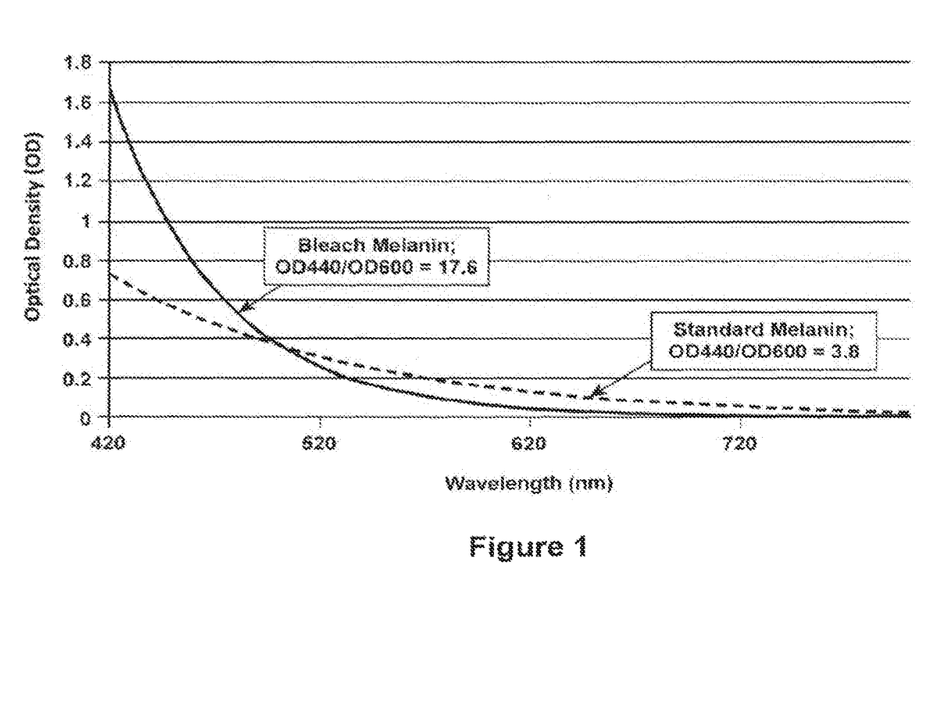
FIG. 1 is a graph comparing the absorbance of standard melanin and a melanin derivative of the present invention over the range of 400-720 nm.

FIG. 1 illustrates the difference in absorption between 420 and 720 nm for a standard melanin and a bleached melanin derivative of the present invention. The spectra show the optical absorption values at different wavelengths of the visible spectrum. At the red end, between 600 nm and 780 nm, both melanins showed relatively low absorption. However, a present melanin derivative absorbs less of the beneficial red light than the standard melanin. Between 400 nm and 500 nm, a present melanin derivative absorbed significantly more of the HEV light than the standard melanin. At 550 nm, the wavelength at which the human eye is most sensitive to is visible light, a present melanin derivative appears lighter than the standard melanin because it absorbs less light.

A melanin derivative useful in the present invention provides the following advantages.

It is generally understood that photochemistry does not occur in the longer-wavelength region, such as the red and near infrared, and it is theorized, but not relied upon, that an increased rate of skin barrier repair is attributed to heat. In this case, red and near infrared (IR) radiation from sunlight and artificial light generate heat because of the absorption of this light by melanin in the skin. A melanin derivative of the present invention protects the skin from HEV light damage and allows the red and near IR wavelength to penetrate the skin and speed skin recovery.

Further, while sunscreen compositions containing additives that absorb UVA and UVB are colorless or white, it has been expected that an additive that absorbs HEV will necessarily impart color to a sunscreen product and generally cause a distortion in the perception of skin tone. This may not be esthetically appealing to the consumer and therefore, it is desirable to use an HEV-absorbing additive that minimally impacts the perception of color changes in skin tones. A melanin derivative used in the present invention achieves this goal. In accord with the above, a present melanin derivative absorbs HEV light strongly, filters the green light moderately, and transmits red and near IR light strongly in order to ensure that red and near IR light reaches sub-epidermal melanin present in the skin, and is converted into heat to contribute to the skin repair rate. Alternatively, the extra transmission of red and near IR light provided by the present melanin derivative is a source of radiant energy for cellular chromophores, such as cytochrome C, which absorbs light in the range from 700 nm to 1200 nm.

The optical absorption of melanins generally increases steadily from the red end of the spectrum to the blue and violet end of the spectrum, and in manner that preserves the perception of color. However, melanins form from different precursors and, when made by different processes, have varying degrees of HEV absorption relative to the absorption of red light. The needs of the sun protection industry require a melanin with a high ratio of blue light absorption to red light absorption, as achieved by a present melanin derivative.

Peroxide bleaching of melanin is known to increase the ratio of blue light absorption to red light absorption. However, peroxide bleaching also is known to decrease the molecular weight of the melanin, which conflicts with another need of skin care industry, i.e., an ingredient in a sunscreen formulation should not penetrate the skin in order to avoid undesirable interactions and to enhance efficacy because physical absorption of light at the surface of the skin is necessary. Skin penetration of an ingredient by molecular diffusion can be mitigated a) by increasing hydrophilicity of the ingredient and/or b) by increasing its molecular weight to 500 Daltons and greater. In accordance with an important feature of the present invention, bleaching techniques create additional carboxyl groups on the melanin derivative, which increase the hydrophilicity of the melanin derivative.

Bleaching with peroxide increases the number of carboxyl units in the covalently-bonded melanin oligomers and thereby increases the hydrophilic character of melanin. Therefore, bleaching reduces the possibility of melanin derivative penetration into the skin. However, it remains necessary to ensure that the molecular weight of the final melanin derivative is 500 Daltons or greater. In accordance with the present invention, this can be accomplished by solvent extraction techniques or dialysis techniques well known to those skilled in the art. These techniques allow removal of the smallest molecular weight fractions, specifically, fractions having a molecular weight below 500 Daltons.

Increasing the blue to red ratio of the optical absorption (optical density) beyond that achieved by bleaching includes solvent extraction/fractionation techniques to produce a more yellow melanin, as described in U.S. Patent Publication 2006/0282066, incorporated herein by reference.

Irrespective of the positive absorption properties of a melanin, no commercial skin protection composition containing a specific light filter for HEV radiation in general, or a melanin derivative in particular, has been introduced. The principal reason for a lack of commercial products containing a melanin is that melanins have a high color thereby causing both the product and treated skin to have limited esthetic appeal, even when melanin synthesis parameters, e.g., oxidizer concentration and reaction temperature, are held constant, the physical character of the product, e.g., color, often varies. The present melanin derivatives overcome this problem, and a preferred embodiment of the present invention incorporates a present melanin derivative into a cosmetic composition, while overcoming the color, esthetic, and formulation problems associated with melanin, thus allowing the use of a melanin derivative to protect skin from HEV light.

The compositions and methods of the present invention are useful in protecting the skin from the effects of HEV radiation, including, for example, premature aging of the skin, wrinkles, fine lines, poor skin tone, and loss of elasticity, and in overcoming a delay in repair of damaged skin attributed to sunlight. The present invention is directed to a method of treating skin comprising topically applying a composition comprising a melanin derivative to skin to protect the skin from the harmful effects of HEV radiation.

The amount of melanin derivative in the composition typically is about 0.01% to about 15%, preferably about 0.05% to about 10%, and more preferably about 0.1% to about 5%, by weight of the composition. The melanin derivative-containing composition typically is admixed with a cosmetically acceptable carrier prior to application to the skin. The cosmetically acceptable carrier can be a liquid, such as water, alcohol, glycol, or natural or synthetic oil, or a powder, such as talc, corn starch, or hydrated silica. The diluting carrier should not cause separation of the melanin derivative from the final composition, or otherwise adversely affect the ability of the melanin derivative to perform its intended function.

More particularly, the cosmetically acceptable carrier can be a liquid, for example, water; an alcohol, such as ethanol, isopropyl alcohol, butanol, or hexanol; a glycol, such as propylene glycol, 1,6-hexadiol, 1,4-butylene glycol, a polyethylene glycol (PEG) or polypropylene glycol (PPG) of molecular weight of about 1000 or less, a PEG-PPG copolymer of molecular weight of about 1000 or less; mineral oil; a natural or synthetic oil commonly used by formulators in the cosmetic arts; or any mixture thereof.

The cosmetically acceptable carrier also can be a particulate solid, typically in powder form. The particulate solid can be a bulking agent commonly use in the cosmetic arts, for example, alumina, aluminum silicate, aluminum stearate, attapulgite, bentonite, calcium carbonate, calcium silicate, cellulose, corn flour, corn meal, corn starch, cotton, dextran, dextrin, diatomaceous earth, Fullers earth, hectorite, hydrated silica, kaolin, magnesium carbonate, magnesium carbonate hydroxide, magnesium silicate, magnesium silicate, magnesium stearate, magnesium sulfate, magnesium trisilicate, microcrystalline cellulose, microcrystalline wax, montmorillonite, oat bran, oat flour, peanut flour, pecan shell powder, potato starch, pumice, rice bran, rice starch, rye flour, silica, silica silylate, silk powder, soy flour, soy protein, talc, tin oxide, titanium dioxide, titanium hydroxide, trimagnesium phosphate, walnut shell powder, wheat bran, wheat flour, wheat starch, zinc oxide, and any mixture thereof. The particulate solids preferably have a particle size of about 200 nm or less in diameter, for example, about 1 to about 200 nm in diameter.

A melanin derivative of the present invention can be added directly to a final composition, or can be admixed with a liquid or solid carrier prior to addition to a final cosmetic or dermatological composition. The melanin derivative can be topically applied to skin after incorporation into a composition containing the carrier and additional ingredients, e.g., a second typically active agent, UVA and/or UVB filters, skin conditioners, and other ingredients typically used in skin care and sunscreen formulations.

A composition containing a present melanin derivative is useful in personal care, cosmetic, and pharmaceutical compositions. The composition can be a sun care composition, after sun care composition, or a general skin care composition. The compositions provide an effective delivery of the melanin derivative to treat the skin, remain on the skin surface, and impart protection against HEV radiation. The resulting compositions for treating skin can be formulated with other topically-applied active compounds, in addition to or in lieu of additional skin protectants to achieve protection against UVB, UVA, and HEV radiation and/or to impart beneficial effects to skin in addition to protection from radiation.

In many embodiments, a compound to protect skin from UVB and/or UVA radiation can be added to the composition. Because both UVA and UVB radiation can be damaging, a preferred sunscreen provides protection from both types of radiation. In such embodiments, the compositions protect all layers of the skin. UVB and/or UVA filters typically are used in sunscreen compositions of the present invention. Sunscreens can be organic or inorganic compounds.

Sunscreens are broadly classified into two categories, i.e., chemical sunscreens and physical sunscreens. Chemical sunscreens absorb UV radiation whereas physical sunscreens act by physically blocking radiation. Chemical sunscreens can be UVA or UVB absorbers. Many sunscreen compositions have a combination of ingredients and may contain both physical and chemical sunscreens. Physical sunscreens, e.g., titanium dioxide and zinc oxide, block both UVA and UVB radiation. A present melanin derivative primarily involves HEV absorption, and therefore is not considered a sunscreen.

Examples of chemical sunscreens include: oxybenzone (benzophenone-3), tannic acid, uric acids, quinine salts, dihydroxy naphtholic acid, an anthranilate, phenylbenzimidazole sulfonic acid, and PEG-25 PABA. Further, sunscreen compounds such as dioxybenzone, cinoxate, ethyl 4-[bis (hydroxypropyl)]aminobenzoate, glyceryl aminobenzoate, homosalate, menthyl anthranilate, octocrylene, octyl methoxycinnamate, octyl salicylate, padimate A, padimate O, red petrolatum, titanium dioxide, 4-menthylbenzylidene camphor, benzophenone-1, benzophenone-2, benzophenone-4, benzophenone-6, benzophenone-12, isopropyl dibenzoylmethane, butyl methoxydibenzoylmethane, zotocrylene, DEA-methoxycinnamate, digalloyl trioleate, TEA-salicylate, or zinc oxide can be used in the present composition.

Therefore, variations on the present compositions include a UV-specific compound to absorb or block UVA and/or UVB radiation to protect the skin. These compounds filter a percentage of the UV spectrum depending on the type, concentration, and intensity of chromophores used.

The filter families include, alone or in combination, and not limited to, the benzotriazoles, benzophenones, benzoic acids/PABA, cinnamates, salicylates, and avobenzones, to further protect the skin against UVA and UVB damage. Maximum loads of one or more UV filters present in a sunscreen composition can be up to 15-30% by weight. A UVA and UVB filter, individually, are present in an amount of about 0.25 to about 3 percent by weight of the composition. When both a UVA and UVB blocker are used, each typically is present in an amount of about 0.5 to about 1.5 percent, by weight.

Additional UV filters, including combinations of any two or more, are selected from the following categories (with specific examples): p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following are additional specific UV filters: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

The sunscreen or dermatological formulations can include a variety of photoactive compounds, preferably including one or more UVA photoactive compound and one or more UVB photoactive compound. In many embodiments, a sunscreen or dermatological formulation includes a photoactive compound selected from the group consisting of: p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and mixtures thereof.

UVA radiation (about 320 nm to about 400 nm) is recognized as contributing to skin damage, particularly to very lightly colored or sensitive skin. A sunscreen or dermatological formulation comprising a dispersion of an HEV-absorbing melanin derivative disclosed herein preferably includes a UVA photoactive compound. Preferably, a sunscreen or dermatological formulation comprising the dispersion of the invention disclosed herein includes a dibenzoylmethane derivative UVA photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

The above described UV filters are commercially available. For example, suitable commercially available organic UV filters are identified by trade name and supplier in Table 1 below:

TABLE 1

| INCI Name | Trade Name | Supplier |
| --- | --- | --- |
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |

TABLE 1-continued

| INCI Name | Trade Name | Supplier |
|---|---|---|
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine | TINOSORB S | Ciba Specialty Chemicals |

Additional UVB and UVA filters are disclosed in U.S. Pat. No. 7,597,825, incorporated herein by reference in its entirety.

In addition to UVB and UVA filters, a present composition also can contain a photostabilizer for the UVB and UVA filters. Photostabilizers include octocrylene, methylbenzilydene camphor, and esters and polyesters of naphthalene dicarboxylic acid. Alkoxy crylenes, and notably methoxy crylenes, are useful photostabilizers. Photostabilizers are disclosed in U.S. Pat. Nos. 6,113,931; 6,284,916; 6,518,451; 6,551,608; 5,576,354; and 7,597,825, each incorporated herein by reference in its entirety.

In accordance with an important feature of the present invention, a topically-applied compound for providing a cosmetic or therapeutic effect, in addition to a compound for protection from radiation, can be any of a wide variety of compounds, either water soluble or oil soluble.

Additional topically-applied active compounds, such as analgesics, anesthetics, anti-acne agents, antibacterial agents, antifungal agents, botanical extracts, pharmaceuticals, minerals, plant extracts, concentrates of plant extracts, exfoliants, emollients, moisturizers, skin protectants, humectants, silicones, skin soothing ingredients, colorants, perfumes, and like can be included in the composition. The quantities of such active compounds present in the composition are sufficient to perform their intended function, without adversely affecting the HEV radiation protection benefits of the composition.

More particularly, such a topically applied active compound can be one of, or a mixture of, a cosmetic compound, a medicinally active compound, a compound used in cosmetics or personal care, or any other compound that is useful upon topical application to the skin. Such topically active agents include, but are not limited to, skin-care compounds, plant extracts, antioxidants, insect repellants, counterirritants, vitamins, steroids, antibacterial compounds, antifungal compounds, anti-inflammatory compounds, topical anesthetics, sunscreens, and other cosmetic and medicinal topically effective compounds.

For example, a skin conditioner can be the topically applied compound. Skin conditioning agents include, but are not limited to, humectants, such a fructose, glucose, glycerin, propylene glycol, glycereth-26, mannitol, pyrrolidone carboxylic acid, hydrolyzed lecithin, coco-betaine, cysteine hydrochloride, glucamine, sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E, and D, selenium and derivatives thereof, amino-functional silicones, ethoxylated glycerin, alpha-hydroxy acids and salts thereof, fatty oil derivatives, such as PEG-24 hydrogenated lanolin, beta-hydroxy acids and salts thereof (e.g., glycolic acid, lactic acid, and salicylic acid), and mixtures thereof. Numerous other skin conditioners are listed in the CTFA Cosmetic Ingredient Handbook, First Ed., J. Nikotakis, ed., The Cosmetic. Toiletry and Fragrance Association (1988), (hereafter CTFA Handbook), pages 79-84, incorporated herein by reference.

The skin conditioner also can be a water-insoluble ester having at least 10 carbon atoms, and preferably 10 to about 32 carbon atoms. Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Suitable esters, therefore, include, for example, but are not limited to:

(a) aliphatic monohydric alcohol esters, including, but not limited to: myristyl propionate, isopropyl isostearate, isopropyl myristate, isopropyl palmitate, cetyl acetate, cetyl propionate, cetyl stearate, isodecyl neopentanoate, cetyl octanoate, isocetyl stearate;

(b) aliphatic di- and tri-esters of polycarboxylic acid, including, but not limited to: diisopropyl adipate, diisostearyl fumarate, dioctyl adipate, a succinate ester, and triisostearyl citrate;

(c) aliphatic polyhydric alcohol esters, including, but not limited to: propylene glycol dipelargonate;

(d) aliphatic esters of aromatic acids, including, but not limited to: C.sub.12-C.sub.15 alcohol esters of benzoic acid, octyl salicylate, sucrose benzoate, and dioctyl phthalate.

Numerous other esters are listed in the CTFA Handbook, at pages 24 through 26, incorporated herein by reference.

The topically applied compound also can be retinoic acid or a retinol derivative.

Similarly, topically applied drugs, like antifungal compounds, antibacterial compounds, anti-inflammatory compounds, topical anesthetics, skin rash, skin disease, and dermatitis medications, and anti-itch and irritation-reducing compounds can be used as the active agent in the compositions of the present invention. For example, analgesics such as benzocaine, dyclonine hydrochloride, aloe vera, and the like; anesthetics such as butamben picrate, lidocaine hydrochloride, xylocaine, and the like; antibacterials and antiseptics, such as povidone-iodine, polymyxin b sulfate-bacitracin, zinc-neomycin sulfate-hydrocortisone, chloramphenicol, ethylbenzethonium chloride, erythromycin, and the like; antiparasitics, such as lindane; essentially all dermatologicals, like acne preparations, such as benzoyl peroxide, erythromycin benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate, and the like; depigmenting agents, such as monobenzone; dermatitis relief agents, such as the active steroid amcinonide, diflorasone diacetate, hydrocortisone, and the like; emollients and moisturizers, such as mineral oil, PEG-4 dilaurate, lanolin oil, petrolatum, mineral wax, and the like; fungicides, such as butocouazole nitrate, haloprogin, clotrimazole, and the like; herpes treatment drugs, such as O-[(2-hydroxymethyl)-methyl]guanine; pruritic medications, such as alclometasone dipropionate, betamethasone valerate, isopropyl myristate MSD, and the like; psoriasis, seborrhea, and scabicide agents, such as anthralin, methoxsalen, coal tar, and the like; steroids, such as 2-(acetyloxy)-9-fluoro-1',2',3',4'-tetrahydro-11-hydroxypregna-1,4-dieno-[16,17-b]naphthalene-3,20-dione and 21-chloro-9-fluoro-1',2',3',4'-tetrahydro-11b-hydroxypregna-1,4-dieno-[16-,17-b]naphthalene-3,20-dione. Any other medication capable of topical administration, like skin protectants, such as allantoin, and anti-acne agents, such as salicylic acid, also can be incorporated in a composition of the present invention in an amount sufficient to perform its intended function. Other topically applied compounds are listed in Remington's Pharmaceutical Sciences, 17th Ed., Mack Publishing Co., Easton, Pa. (1985), pages 773-791 and pages 1054-1058 (hereinafter Remington's), incorporated herein by reference.

The topically active compound also can be a plant extract or natural oil. Preferred plant extracts and natural oils absorb blue light and generally have a yellow, yellow-brown, or red color. Numerous plant extracts are available from Lipo Chemicals, Inc. Paterson, N.J. Nonlimiting plant extracts are those obtained from alfalfa, aloe vera, amla fruit, angelica root, anise seed, apple, apricot, artichoke leaf, asparagus root, banana, barberry, barley sprout, bee pollen, beet leaf, bilberry fruit, birch leaf, bitter melon, black currant leaf, black pepper, black walnut, blueberry, blackberry, burdock, carrot, cayenne, celery seed, cherry, chickwood, cola nut, corn silk, cranberry, dandelion root, elderberry, eucalyptus leaf, flax oil powder, ginger root, gingko leaf, ginseng, goldenrod, goldenseal, grape, grapefruit, guava, hibiscus, juniper, kiwi, kudzu, lemon, licorice root, lime, malt, marigold, myrrh, olive leaf, orange fruit, orange peel, oregano, papaya fruit, papaya leaf, passion fruit, peach, pear, pine bark, plum, pomegranate, prune, raspberry, rhubarb root, rosemary leaf, sage leaf, spearmint leaf, St. John's wart, strawberry, sweet cloves, tangerine, violet herb, watercress, watermelon, willow bark, wintergreen leaf, witch hazel bark, yohimbe, and yucca root. An example of a natural oil is rice bran oil.

A composition of the present invention is prepared by admixing the melanin derivative with other ingredients traditionally included in cosmetic, dermatological, medicinal, and other such compositions. These ingredients include, but are not limited to, dyes, fragrances, preservatives, antioxidants, detackifying agents, and similar types of compounds. The ingredients are included in the composition in an amount sufficient to perform their intended function.

The following additional ingredients typically are included in a present composition. Each of these ingredients, and any other ingredient, is present in a sufficient amount to perform its intended function, without adversely affecting the efficacy of melanin derivative with respect to treating skin for protection against HEV radiation.

For example, a present composition can contain a surfactant. The surfactant can be an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

Examples of anionic surfactants include, without limitation, soaps, alkyl sulfates, anionic acyl sarcosinates, methyl acyl taurates. N-acyl glutamates, acyl isethionates, alkyl phosphate esters, ethoxylated alkyl phosphate esters, alkyl sulfosuccinates, trideceth sulfates, protein condensates, mixtures of ethoxylated alkyl sulfates, and the like. Examples of anionic nonsoap surfactants include, without limitation, the alkali metal salts of an organic sulfate having an alkyl radical containing about 8 to about 22 carbon atoms and a sulfonic acid or sulfuric acid ester radical. Examples of zwitterionic surfactants include, without limitation, derivatives of aliphatic quaternary ammonium, phosphonium, and sulfonium compounds, in which the aliphatic radicals can be straight chain or branched and wherein one of the aliphatic substituents contains an anionic water-solubilizing group, e.g., carboxyl, sulfonate, sulfate, phosphate, or phosphonate. Examples of amphoteric surfactants include, without limitation, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxyl, sulfonate, sulfate, phosphate, or phosphonate. Examples of cationic surfactants include, without limitation, stearyldimethylbenzyl ammonium chloride; dodecyltrimethyl ammonium chloride; nonylbenzylethyldimethyl ammonium nitrate; and tetradecylpyridinium bromide. Nonionic surfactants include, without limitation, compounds produced by the condensation or ethylene oxide groups with an organic hydrophobic compound, which may be aliphatic or alkyl aromatic in nature, for example, the polyethylene oxide condensates of alkyl phenols.

A present composition also can contain a hydrotrope. A hydrotrope is a compound that has an ability to enhance the water solubility of other compounds. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, sodium camphor sulfonate, and disodium succinate.

A present composition also can contain an organic solvent, for example, as a component of the cosmetically acceptable carrier. The solvent can be a water-soluble organic compound containing one to six, and typically one to three, hydroxyl groups, e.g., alcohols, diols, triols, and polyols. Specific examples of solvents include, but are not limited to, methanol, ethanol, isopropyl alcohol, n-butanol, n-propyl alcohol, propylene glycol, glycerol, diethylene glycol, dipropylene glycol, tripropylene glycol, hexylene glycol, butylene glycol, 1,2,6-hexanetriol, sorbitol, PEG-4, 1,5-pentanediol, similar hydroxyl-containing compounds, and mixtures thereof. The solvent also can be water or an aprotic solvent, e.g., dimethyl sulfoxide or tetrahydrofuran.

A present composition also can contain a thickening or gelling agent. A thickening or gelling agent can be, for example, a polymer that is water soluble or that generates a colloidal solution in water. A thickening or gelling agent, therefore, can be, for example, polymers or copolymers unsaturated carboxylic acids or unsaturated esters, polysaccharide derivatives, gums, colloidal silicates, polyethylene glycols (PEG) and their derivatives, polyvinylpyrrolidones and their derivatives, polyacrylamides and their derivatives, polyacrylonitriles, hydrophilic silica gels, or mixtures thereof.

Specific thickening or gelling agents can be, for example, acrylic and/or methacrylic polymers or copolymers, vinylcarboxylic polymers, polyglyceryl acrylates or methacrylates, polyacrylamides derivatives, cellulose or starch derivatives, chitin derivatives, alginates, amino acids, ceramides, fatty acids, cholesterol and derivatives thereof, and other natural moisturizing compounds, hyaluronic acid and its salts, chondroitin sulphates, xanthan, gellan, Rhamsan, karaya or guar gum, carob flour, and colloidal aluminum magnesium silicates of the montmorillonite type.

Additional thickening or gelling agents include vinylcarboxylic polymers sold under the tradename CARBOPOL® (Lubrizol/Noveon), acrylic acid/ethyl acrylate copolymers, acrylic acid/stearyl methacrylate copolymers, carboxymethylcellulose, hydroxymethylcellulose, hydroxypropylcellulose, microcrystalline cellulose, hydroxypropyl guar, colloidal hectorites, bentonites, and the like.

The present compositions also can contain pigments, dyes, preservatives, hydrating agents, and the like.

The pigments can be inorganic pigments, organic pigments, or nacreous pigments. Inorganic pigments include, but are not limited to, titanium dioxide, black, yellow, red or brown iron oxide, manganese violet, ultramarine violet, ultramarine blue, chromium oxide, and the like. Among organic pigments, nonlimiting examples include D & C Red No. 3, No. 6, No. 7, No. 9, No. 13, No. 19, No. 21, No. 27, No. 30, or No. 36, or alternatively carbon black.

The nacreous pigments can be, for example, white nacreous pigments, such as mica coated with titanium oxide or with bismuth oxychloride. Colored nacreous pigments, such as titanium mica colored with iron oxides or with chromium oxide, titanium mica colored with an organic pigment of the above-mentioned type, or alternatively, nacreous pigments based on bismuth oxychloride, also can be used.

The dye can be, for example, a water-soluble dye, such as Ponceau disodium salt, alizarin green disodium salt, quinoline yellow, amaranth trisodium salt, tartazine disodium salt, rhodamine monosodium salt, fuchsin disodium salt, xanthophylls, and the like.

The present compositions also can contain fillers, especially clays of the montmorillonite, hectorite, or bentonite type, or other fillers, such as silicas, silicone powders, polyamides, or powdered polymethyl methacrylate. Various white fillers such as, for example, talc, kaolin, powdered TEFLON® (polytetrafluoroethylene), powdered polyethylene, powdered crosslinked poly-beta-alanine, and the like, also are useful.

Other classes of optional ingredients included in a present composition can be, but not limited to, pH adjusters, chelating agents, preservatives, buffering agents, foam stabilizers, opacifiers, and similar classes of ingredients known to persons skilled in the art. Specific optional ingredients include inorganic phosphates, sulfates, and carbonates as buffering agents; EDTA and phosphates as chelating agents; and acids and bases as pH adjusters.

Nonlimiting examples of basic pH adjusters are ammonia; mono-, di-, and tri-alkyl amines; mono-, di-, and tri-alkanolamines; alkali metal and alkaline earth metal hydroxides; and mixtures thereof. Specific, nonlimiting examples of basic pH adjusters are ammonia; sodium, potassium, and lithium hydroxide; monoethanolamine; triethylamine; isopropanolamine; diethanolamine; and triethanolamine. Examples of acidic pH adjusters are the mineral acids and organic carboxylic acids. Nonlimiting examples of mineral acids are citric acid, hydrochloric acid, nitric acid, phosphoric acid, and sulfuric acid.

The melanin derivative can be incorporated into compositions designed as cosmetic basecoats and undercoats, blushers, face, body, and hand creams and lotions, cosmetic foundations, hormone creams and lotions, leg and body paints, makeup bases, makeup fixatives, makeup products, moisturizing creams and lotions, paste masks, skin care products, skin fresheners, skin lighteners, tonics, dressings, and wrinkle smoothing creams and lotions.

In particular embodiments, the melanin derivative can be incorporated into lotions; makeup preparations, like makeup foundations; skin care preparations, like hand lotions, sunscreens, body lotions, baby lotions, baby creams, facial creams, moisturizing lotions, makeup removers, anti-acne preparations, antiaging preparations, and sebum control; analgesic and cortisonal steroid creams and preparations; insect repellants; and facial masks and revitalizers.

A composition containing the melanin derivative can be in the form of a solution, an oil-in-water emulsion, a water-in-oil emulsion, a gel, a dispersion, a stick, a mousse, a microemulsion, a nanoemulsion, or other product form known in the skin care and dermatological arts. The melanin derivative also can be delivered from an encapsulated or non-encapsulated delivery system, a liposome, or other vesicle or lamellar delivery system. The composition form can be, for example, a liquid form, e.g., a solution, a gelled solution, or a suspension in an aqueous or oily medium; or a semi-liquid formulation, e.g., a cream, a gel, a paste, an ointment, a salve, a liposome, an emulsion, or a microemulsion.

A composition of the present invention is topically applied to the skin as needed in order to protect the skin against the harmful effects of HEV radiation. Typically, the composition is topically applied to the skin one to four times per day. However, application of a present composition can be more or less frequent as prescribed, required, or desired. The present compositions are applied to the skin by spraying or rubbing. The preferred route of administration is rubbing onto the skin with a soft massage to ensure intimate contact with the skin.

In addition to protecting skin from the effects of HEV light, a present melanin derivative also can protect light-sensitive compounds in a composition from light degradation. A "light-sensitive compound" degrades when exposed to light, for example, sunscreen compounds and anti-oxidants, like avobenzone, oxybenzone, vitamin A and its derivatives, vitamin D, tocopherols, hydroquinone, kojic acid, ascorbic acid and its derivatives, natural plant extracts, licorice extract, blueberry extract, and mixtures thereof. In particular, a present melanin derivative can impart photostability to topically active compounds in a composition by either photochemical or photophysical interactions. Melanin is known to interact with and sequester a variety of reactive oxygen species (ROS) created by the absorption of UV and HEV light by such photosensitive compounds. These photochemical by-products can destroy these sensitive compounds in the absence of adsorption and stabilization by the melanin derivative.

Melanin is known to photostabilize nearby molecules by photophysical means as well. Melanin can quench the fluorescence of photosensitive compounds codissolved in a composition, such as a sunscreen composition, thereby reducing the lifetime of the compound in the significantly more reactive excited state. Another photophysical mechanism by which melanin provides photostability is singlet oxygen quenching.

The present melanin derivatives likewise can stabilize light-sensitive compounds in a composition by adding a sufficient amount of the melanin derivative to the composition, typically in an amount of about 0.001% to 0.1%, by weight, of the composition. A composition is also disclosed comprising about 0.001% to about 1%, by weight, of a melanin derivative, a cosmetically acceptable carrier and a light-sensitive compound.

Another aspect of the present invention is use of a present melanin derivative to reduce the photosensitizing effect of various particulate solids. For example, it is known that small particle size titanium dioxide, i.e., about 200 nm or less, provides a maximum protection against sunlight. However, at such small particle sizes, titanium dioxide also is a skin photosensitizer. It has been found that including a present melanin derivative in compositions containing small particle size particles, like titanium dioxide, at least partially overcome the photosensitizing effects of such particles.

Another aspect of the present invention is formulation of a present melanin derivative with a carotenoid. The resulting composition provides enhanced protection of the skin against the harmful effects of sunlight. Further, the overall natural color of skin includes carotene. Examples of carotenes useful in the present invention include, but are not limited to, lutein, zeaxanthin, beta-carotene, alpha-carotene, gamma-carotene, beta-cryptoxanthin, lycopene, astaxanthin, capsathin, capsorubin, and mixtures thereof. Also envisioned are other naturally occurring and synthetic xanthophylls and carotenes.

To demonstrate the new and unexpected benefits provided by the present invention, the following compositions were prepared. The appearance of each composition was noted, and the absorbance spectra were taken and analyzed. The melanin derivative included in the compositions had a molecular weight of about 7000 Daltons, an OD (440 nm)/OD (660 nm) ratio of 17, and varied in color from yellow to orange-brown (in Example 1) and yellow to black (in Example 2), as the amount of melanin derivative in the composition was increased over the range of 0.001% to 15%, by weight.

Example 2: Emulsion Formulation

| SEQUENCE[1] | PERCENT | INGREDIENT | INCI NAME |
|---|---|---|---|
| 1 | 83.94 | Deionized Water | Water |
| 1 | 0.10 | Disodium EDTA | Disodium EDTA |
| 1 | 0.11 | CARBOPOL ® Ultrez 10 (2) | Carbomer |
| 2 | 0.10 | Keltrol CG | Xanthan Gum |
| 2 | 1.00 | Preservative | |
| 3 | 2.75 | LIPO ® GMS 450 (1) | Glyceryl Stearate |
| 3 | 1.25 | LIPOCOL ® C (1) | Cetyl Alcohol |
| 3 | 1.00 | LIPOPEG ® 39-S (1) | PEG-40 Stearate |
| 3 | 0.50 | LIPOWAX ® P (1) | Cetearyl Alcohol (and) Polysorbate 60 |
| 3 | 8.00 | LIPONATE ® GC (1) | Caprylic/Capric Triglyceride |
| 4 | 0.25 | NaOH (18% Sol.) | Sodium Hydroxide |
| 5 | 1.00 | Aqueous solution of a Melanin Derivative (10% Active) | |
| | 100.00 | | |

(1) Lipo Chemicals, Inc.
(2) Lubrizol
Viscosity of approximately 20,000 cps
[1]Premixes and order of addition of composition ingredients.

Example 3: Gel Formulation

| SEQUENCE[1] | PERCENT | INGREDIENT | INCI NAME |
|---|---|---|---|
| 1 | 75.98 | Deionized Water | Water |
| 2 | 0.10 | Disodium EDTA | Disodium EDTA |
| 2 | 20.00 | CARBOPOL ® 980 (2% Sol.) (2) | Carbomer |
| 2 | 1.00 | LIPONIC ® EG-1 (1) | Glycereth-26 |
| 3 | 0.92 | Sodium Hydroxide (18% Sol.) | Sodium Hydroxide |
| 4 | 1.00 | Preservative | |
| 5 | 1.00 | Aqueous solution of a Melanin Derivative (10% Active) | |
| | 100.00 | | |

Viscosity of approximately 20,000 cps

The following formulations also can contain greater amounts of the melanin derivative (added as a 10% by weight aqueous solution), as needed or desired.

| SEQUENCE[1] | PERCENT | INGREDIENT | INCI NAME |
|---|---|---|---|
| 1 | 72.24 | Deionized Water | Water |
| 1 | 2.50 | Glycerin (119) | Glycerin |
| 1 | 0.25 | Xanthan Gum | Xanthan Gum |

-continued

| SEQUENCE[1] | PERCENT | INGREDIENT | INCI NAME |
|---|---|---|---|
| 2 | 5.00 | LIPOMULSE ® Luxe (1) | Cetearyl Alcohol (and) Glyceryl Stearate (and) PEG-40 Stearate (and) Ceteareth-20 |
| 2 | 20.00 | LIPOVOL ® MOS-130 (1) | Tridecyl Stearate (and) Tridecyl Trimellitate (and) Dipentaerythrityl Hexacaprylate/Hexacaprate |
| 3 | q.s. | Preservative | |
| 4 | 0.1 | Melanin Derivative | |
| | 100.00 | | |

(1) Lipo Chemicals, Inc.

In the main kettle, combine Sequence 1 ingredients and heat to 78-80.degree. C.

Heat Sequence 2 ingredients to 80.degree. C. add to Sequence 1 ingredients and mix well. Slowly add Sequence 3 ingredient to the mixture with medium to high speed propeller mixing. As composition thickens, increase mixing speed.

Cool to 40.degree. C., add Sequence 4 ingredient then adjust pH to 6.0-7.0 with 10% citric acid solution. Cool to 25.degree. C.

Viscosity: TF at 3 rpm-245,000 cps.

Example 5: Liquid Make-Up Formulation

| SEQUENCE[1] | PERCENT | INGREDIENT | INCI NAME |
|---|---|---|---|
| 1 | 72.24 | Deionized Water | Water |
| 1 | 0.40 | VEEGUM ® HV (4) | Magnesium Aluminum Silicate |
| 1 | 0.20 | CMC 7MF (2) | Sodium Carboxymethyl Cellulose |
| 1 | 4.60 | Propylene Glycol (4) | Propylene Glycol |
| 2 | 0.20 | ALCOLEC ® Z7 (5) | Hydroxylated Lecithin |
| 2 | 8.00 | TRONOX ® CR-837 (6) | Titanium Dioxide (CI77891) |
| 2 | 0.50 | Iron Oxide Red (3) | Iron Oxides (CI 77489) |
| 2 | 1.00 | Iron Oxide Yellow (3) | Iron Oxides (CI 77489) |
| 2 | 0.20 | Iron Oxide Black (3) | Iron Oxides (CI 77489) |
| 2 | 3.00 | ORGASOL ® Caresse (1) | Polyamide-5 |
| 3 | 15.00 | LIPOVOL ® MOS-70 (1) | Tridecyl Stearate (and) Neopentyl Glycol Dicaprylate/Dicaprate (and) Tridecyl Trimellitate |
| 3 | 1.50 | LIPOSORB ® S-20 (1) | Polysorbate 60 |
| 3 | 3.50 | LIPOMULSE ® Luxe (1) | Cetearyl Alcohol (and) Glyceryl Stearate (and) PEG-40 Stearate (and) Ceteareth-20 |
| 4 | q.s | Preservative | |
| 5 | 0.1 | Melanin Derivative | |
| | 100.00 | | |

(1) Lipo Chemicals, Inc.
(2) Aqualon
(3) Hilton Davis
(4) Ruger Chemical Co., Inc.
(5) American Lecithin Company
(6) Tronox, Inc.

In main kettle, combine water and Veegum HV under propeller mixing, heating to 75-80.degree. C., mix at temperature for 30 minutes.

Slowly add remaining Sequence 1 ingredients to main vessel with medium speed propeller mixing.

Slowly add Sequence 2 ingredients to main vessel with medium speed propeller mixing.

Pass combined Sequence 1 and 2 ingredients through colloid mill and recirculate until pigments are evenly dispersed.

Transfer the bulk to main kettle, mix slowly under propeller mixing, and heat to 80-85.degree. C.

In auxiliary kettle, combine Sequence 3 ingredients under propeller mixing and heat to 75-80.degree. C.

At a proper temperature of 75-80.degree. C. add combined Sequence 3 ingredients to the batch with propeller mixing, while maintaining the temperature until emulsion is complete. Begin cooling to 40.degree. C. Switch to slow sweep mixing as batch thickens.

At 40.degree. C., add Sequence 4 ingredient, followed by Sequence 5 ingredient. Adjust pH to 6.0 to 7.0 with 10% citric acid solution.

Cool to 30.degree. C., pour the batch into a suitable container.

Example 6: SPF 50 Sunscreen Lotion Formulation

| SEQUENCE[1] | PERCENT | INGREDIENT | INCI NAME |
|---|---|---|---|
| 1 | 54.59 | Deionized Water | Water |
| 1 | 0.10 | Carbopol Ultrez 10 | Carbomer |
| 1 | 0.10 | Disodium EDTA | Disodium EDTA |
| 1 | 1.50 | LIPONIC ® EG-1 (1) | Glycereth-26 |
| 2 | 4.50 | LIPOMULSE ® Luxe (1) | Cetearyl Alcohol (and) Glyceryl Stearate (and) PEG-40 Stearate (and) Ceteareth-20 Stearate |
| 2 | 7.50 | Neo Heliopan Type AV (2) | Ethylhexyl Methoxycinnamate (Octinoxate) |
| 2 | 5.00 | Neo Heliopan Type OS (2) | Ethylhexyl Salicylate (Octisalate) |
| 2 | 4.00 | Neo Heliopan Type BB (2) | Benzophenone-3 (Oxybenzone) |
| 2 | 10.00 | Neo Heliopan Type 303 (2) | Octocrylene |
| 2 | 2.50 | Ganex V220 (5) | VP/Eicosene Copolymer |
| 2 | 1.00 | PANALANE ® L-14E (3) | Hydrogenated Polyisobutene |
| 2 | 0.10 | Vitamin E Acetate (4) | Tocopheryl Acetate |
| 2 | 9.00 | LIPONATE ® NEB (1) | C12-15 Alkyl Benzoate |
| 3 | 0.10 | Sodium Hydroxide (18% sol.) | Sodium Hydroxide |
| 4 | q.s. | Preservative | |
| 5 | 0.1 | HEV Melanin (1) | |
| | 100.00 | | |

(1) Lipo Chemicals, Inc.
(2) Symrise
(3) Lipo (Ineos)
(4) Ruger Chemical Co.
(5) ISP In a main kettle, weigh out the water, add Ultrez 10 and begin heating to 75-80.degree. C. with propeller agitation.

Mix for 30 minutes or until no gel lumps are visible, then add the rest of Sequence 1 ingredients and maintain heat at 75-80.degree. C. with propeller mixing.

In a side kettle, combine Sequence 2 ingredients, heat to 75-80.degree. C., and mix until uniform.

Slowly add Sequence 2 ingredients to Sequence 1 ingredients and mix until emulsification is complete.

Add Sequence 3 ingredient to the batch as a neutralizing agent and mix well. Cool to 40.degree. C. with mixing. Add Sequence 4 ingredient, followed by Sequence 5 ingredient. Adjust pH to 6.0-7.0 with 10% citric acid solution, cool to 25.degree. C.

To further demonstrate the benefits of a present melanin derivative, the effect of a melanin derivative on various genes exposed to blue light was examined. The melanin derivative utilized in the gene expression tests was an approximately 10 wt % aqueous solution having L*a*b* values of L—about 89 to about 92, a—about 0.25 to about 3, and b—about 40 to about 53; an OD (440 nm)/OD (600 nm) ratio of about 17, and a molecular weight of about 7000 Daltons.

It is well known that when a gene is activated and expressed, RNA is produced. Gene expression technologies measure the amount of a specific RNA in a given cell or tissue. It also is well known that lifestyle, aging, disease, and other conditions influence the regulation of specific genes.

In this test, the quantitative polymerase chain reaction (qPCR) process was used. Each target gene is amplified using a set of primers and a fluorescent labeled probe that contain complementary sequences (DNA code) to the gene of interest. The probe contains a fluorescent reporter dye (R) on one end and a quencher dye (Q) that inhibits the fluorescent signal. DNA amplification occurs with the addition of a DNA polymer (Taq polymerase). The primers are gene sequence specific and serve as signals that initiate the amplification process at a specific cDNA site. As the DNA synthesis reaction proceeds, the quencher is displaced from the probe, causing an increase in fluorescent signal. A detection instrument reads the level of fluorescence in each well every 7 seconds and records this data in real time. Samples with greater amounts of starting material produce more copies of DNA and emit greater levels of fluorescence.

Figure 2:
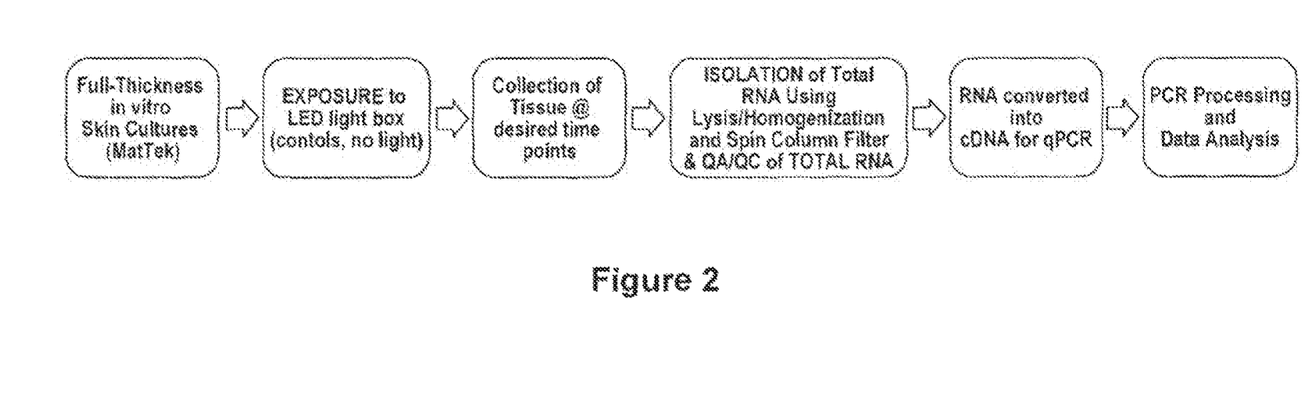
FIG. 2 is a schematic diagram of the gene expression studies.

A schematic of the gene expression study process is provided in FIG. 2. FIG. 2 shows that EPIDERM® full thickness skin was exposed to HEV light for 12, 24, and 72 hours. qPCR was used to measure changes in target genes of each culture. Most of significant expression changes were observed after 72 hours, thereby suggesting the role of ROS mediation process. Some of the target genes showed significant down or up regulation, meaning decrease or increase in expression, respectively. The results are illustrated in Table 1.

| | Gene name | Change with exposure to blue light | Change with exposure to blue light and HEV Melanin Derivative | Meaning of the data |
|---|---|---|---|---|
| Stratum corneum | Keratin 1 (KRT1) | ⇓ | ⇔ | HEV light may be slowing differentiation and maturation of keratinocytes to corneocytes leaving more cells in a senescence state (aging) and slowing the renewal of the stratum corneum, which may lead to reduction in skin barrier function. |

| Gene name | | Change with exposure to blue light | Change with exposure to blue light and HEV Melanin Derivative | Meaning of the data |
|---|---|---|---|---|
| Stratum corneum and Living epidermis | Cytokeratin 10 (KRT10) | ↓ | — | KRT10 encodes for keratin filaments, regulates tissue development and differentiation. Plays an important role in the renewal of the stratum corneum. Down regulation by blue light can over time leads to weakening the skin barrier making th skin more fragile |
| Living epidermis | Nuclear factor kappa B inhibitor (NFKBIA) | ↓ | — | NFKB is a transcription factor that stimulates the expression of over 150 genes including inflammation and cancer genes. It is associated with chronic skin disorders, such as psoriasis and dermatitis. Exposure to blue light induces the NFKB system (the inhibitor is down regulated) which is associated with chronic inflammation and cancer |
| Living epidermis and dermis | Dermatopontin (DPT) | ↓ | — | In the skin, DPT promotes epidermal keratinocytes adhesion. Down regulation of DPT by the light damages the connections between keratinocytes making the skin barrier weaker. It is also reducing collagen production and skin elasticity. |
| Living epidermis and dermis | Heat shock protein A1A (HSPA1A) | — | ↑ | HSP assists other proteins to assemble correctly under stress conditions, such as irradiation and oxidative insult. Protection involves damage prevention and DNA repair. Irradiating the skin with blue light did not activate the gene. It was only activated with the protection of the melanin derivative |
| Living epidermis and dermis | Proopiomelanocortin (POMC) | ↓ | — | POMC is a precursor for alpha melanocyte stimulating hormone (a-MSH), which is expressed in melanocytes, keratinocytes, and fibroblasts. A-MSH regulates melanin production via stimulating of tyrosinase and affects melanocytes dendricity and proliferation. Decrease in POMC can lead to reduction in melanin production, decreased skin immunity, and uneven pigmentation. |
| Dermis | Elastin (ELN) | ↓ | — | Elastin contributes to the elasticity and firmness of the dermis. Reduction in elastin levels can lead to reduced skin flexibility, wrinkles, and sagging |
| Dermis | Metaloproteinase 1 (MMP1) | ↑ | — | Also known as collagenase. Cleaves structural collagens. Elevation in MMP1 levels corresponds with destruction of the dermis, leading over time to wrinkles and sagging. |

↓ Down regulation
↑ Up regulation
— Unchanged

The gene expression study demonstrates the effect of HEV light on key aging and inflammatory gene expressions in the skin leading to the following harmful effects: weak barrier function and fragility; elevation is senescent cells; harmful effect to essential proteins that may lead to depressed immunity, inflammation and cancer; uneven pigmentation; and destruction of the dermal fiber network that over time can be expressed in wrinkles and skin sagging A present melanin derivative was shown in this study to protect skin against these harmful effects.

Obviously, many modifications and variations of the invention as hereinbefore set forth can be made without departing from the spirit and scope thereof and, therefore, only such limitations should be imposed as are indicated by the appended claims.

What is claimed is:

1. A method of protecting and repairing mammalian skin from effects of high energy visible ("HEV") radiation comprising contacting the skin in need thereof with a composition comprising:

(a) about 0.01% to about 15%, by weight, of a melanin derivative having a high HEV absorption and a low absorption of red light; which is characterized by a ratio of optical density at 440 nm to optical density at 600 nm of 10 or greater, and a molecular weight of 500 to about 10,000 Daltons; and (b) a cosmetically acceptable carrier.

2. The method of claim 1 wherein the carrier comprises a liquid or a powder.

3. The method of claim 1 wherein the melanin derivative remains on a surface of the skin.

4. The method of claim 1 wherein the composition is in a form of a solution, a dispersion, an emulsion, a stick, a mousse, or a gel.

5. The method of claim 1 wherein the composition protects the skin by reducing a risk of skin photo-aging and premature skin aging.

* * * * *